United States Patent [19]

Murtha

[11] 4,219,689

[45] Aug. 26, 1980

[54] AROMATIC HYDROALKYLATION CATALYST USING IRIDIUM ON ZEOLITES

[75] Inventor: Timothy P. Murtha, Bartlesville, Okla.

[73] Assignee: Phillips Petroleum Company, Bartlesville, Okla.

[21] Appl. No.: 940,807

[22] Filed: Sep. 8, 1978

[51] Int. Cl.$^2$ ............................................... C07C 3/52
[52] U.S. Cl. .................................................. 585/425
[58] Field of Search ........................................ 585/425

[56] References Cited

U.S. PATENT DOCUMENTS

| | | | |
|---|---|---|---|
| 3,437,586 | 4/1969 | Weisz | 208/110 |
| 3,509,042 | 4/1970 | Miale | 208/120 |
| 3,784,617 | 1/1974 | Suggitt et al. | 585/425 |
| 3,839,477 | 10/1974 | Suggitt et al. | 585/425 |

Primary Examiner—Veronica O'Keefe

[57] ABSTRACT

Aromatic hydrocarbons are contacted under hydroalkylation conditions and in the presence of hydrogen, with a catalyst comprising an iridium compound supported on a calcined, acidic, nickel and rare earth-treated crystalline zeolite.

8 Claims, No Drawings

AROMATIC HYDROALKYLATION CATALYST USING IRIDIUM ON ZEOLITES

This invention relates to a composition useful as a catalyst for hydroalkylation of aromatic hydrocarbons. In accordance with another aspect, this invention relates to a process for the hydroalkylation of aromatic hydrocarbons to produce cycloalkyl aromatic hydrocarbons by contacting with a catalyst comprising iridium supported on a calcined, acidic, nickel and rare earth-treated crystalline zeolite. In accordance with a further aspect, this invention relates to a catalyst composition comprising iridium supported on a calcined, acidic nickel and rare earth-treated crystalline zeolite.

Prior art catalysts in the field of hydroalkylation processes suffered from several drawbacks. These deficiencies of the prior art catalysts for the hydroalkylation reaction included: (1) The use of support materials for certain catalysts which are not able to withstand the temperatures employed in a typical air burn-off regeneration operation. Such regeneration operates are commonplace in the catalytic art for hydrocarbon conversions of various types and it is highly desirable that the catalyst for the hydroalkylation process be stable to such typically employed regeneration conditions. (2) Productivity is rather low as judged by the low liquid hourly space velocities (LHSV) that are utilized in the prior art. Thus a more active and more selective hydroalkylation catalyst is desired. (3) A number of the catalysts of the prior art for the hydroalkylation reaction are prepared by very complex and time consuming processes. For example, starting with a powdered crystalline zeolite support, said support is cation exchanged, washed and then incorporated into a matrix of another material such as silica-alumina. This combination is calcined, cooled, and impregnated with certain metal salts. Finally the composite is extruded into pellets and the like. Thus it is desirable that a more simplified and less expensive process for making active and selective catalysts be found. (4) Certain catalysts of the prior art for the hydroalkylation reaction were of fixed acidity because of the type of support material utilized. This left little variation that could be made in this important property of the hydroalkylation catalyst. It is therefore desirable that catalysts be developed which are varied easily in their acidity characteristics.

Accordingly, an object of this invention is to provide an improved process for the hydroalkylation of aromatic compounds.

Another object of this invention is to provide a catalyst composition effective for the hydroalkylation of aromatic compounds.

Another object of this invention is to provide a composition useful as a catalyst in hydroalkylation reactions which are simpler and less expensive to produce as compared to prior art catalysts.

Other objects, aspects, as well as the several advantages of the invention will be apparent to one skilled in the art upon reading the specification and the appended claims.

According to the invention, at least one aromatic hydrocarbon is contacted under hydroalkylation conditions and in the presence of hydrogen with a composition comprising iridium supported on a nickel and rare earth-treated crystalline zeolite support which is calcined to produce an acidic support before or after impregnation with an iridium compound. Such a composition when used as a catalyst is regenerated by air burn-off and is a highly active and selective catalyst.

Further according to the invention, a composition is provided comprising at least one iridium compound supported on a calcined, acidic, nickel and rare earth-treated crystalline zeolite.

In accordance with one specific embodiment of the invention, benzene is converted to cyclohexylbenzene in high yields by contacting with a catalyst composition comprising iridium supported on a calcined, acidic, nickel and rare eath-treated crystalline zeolite.

The composition of the instant invention can be briefly described as a crystalline zeolite which has been cation exchanged with rare earth, nickel and ammonium compounds followed by a calcination step and an iridium compound impregnation step wherein the iridium compound or mixture thereof is impregnated on the cation exchanged zeolite to give the final composition either before or after the calcination step. Although not absolutely necessary, it is preferred that the above catalyst be treated with hydrogen prior to introduction of the aromatic hydrocarbon feed in the hydroalkylation process of improved results.

The compositions of the instant invention are useful as catalysts and to some extent solve or obviate each of the above-mentioned deficiencies of the prior art catalyst. For example, the supports utilized for the compositions of the instant invention are stable to regeneration conditions utilized under typical air burn-off operations; they appear to operate at higher levels of productivity in that they show a higher degree of activity and selectivity than certain of the prior art catalysts; the process of making the compositions of the instant invention is simple and straightforward and the compositions thus obtained should be less expensive than those of the prior art which utilize very complex steps in their preparation; and the compositions of the instant invention can be made with a high degree of flexibility in the degree of acidity simply by adjusting the cation exchange conditions on the crystalline zeolite support utilized for the compositions of this invention.

The support material for the composition employed in the instant invention is a crystalline zeolite which has been treated under cation exchange conditions with a mixture of rare earth, nickel and ammonium compounds such that the cation metal content of the support is partially exchanged. Generally the cationic metal is an alkali metal which is sufficiently removed by cation exchange such that the remaining alkali metal content after the cation exchange step ranges from about 0.01 to about 2 percent by weight. Some of the more commonly employed crystalline zeolites which are suitable for use in accordance with the present invention are the Type X or Type Y crystalline zeolites which are sometimes called molecular sieves because of their essentially uniform pore diameters. Some suitable Type Y synthetic crystalline zeolites are described for example in U.S. Pat. No. 3,130,007 and some suitable Type X zeolites are described in U.S. Pat. No. 2,882,244. Such materials are presently commercially available as for example zeolites SK-40 (Type Y) and 13X (Type X) from the Linde Division of Union Carbide Corporation, New York, N.Y.

The alkali metal form of the crystalline zeolites usually comprises sodium as the alkali metal and said zeolites are treated under cation exchange conditions with a mixture of rare earth, nickel and ammonium compounds in accordance with the present invention in order to provide a suitable support material for use in the preparation of the compositions of the invention.

It is contemplated that any of the readily available rare earth metal compounds can be employed in the cation exchange solution. Generally, the compounds used are those in which the rare earth metal-containing ion is present in the cationic state. Representative rare earth metal compounds include nitrates, bromides, acetates, chlorides, iodides, sulfates and mixtures thereof of one or more of the rare earth metals including cerium, lanthanum, praseodymium, neodymium, samarium, europium, gadolimium, terbium, dysposium, holmium, erbium thulium, ytterbium, and lutetium. Compounds of the rare earths named above may be employed singly; however, it is often convenient to employ mixtures of the rare earths as these are commercially available. For example, mixtures of rare earth metal compounds such as the chlorides of lanthanum, cerium, praseodymium, neodymium, samarium and gadolimium are available commercially at a relatively low cost and may be effectively employed.

As noted above, the zeolite material is cation exchanged with a mixture of rare earth, nickel and ammonium compounds according to the instant invention. Any convenient ammonium compound may be employed although the chloride is preferred because it is inexpensive and readily available. The weight ratio of ammonium compound to nickel and rare earth compounds in the aqueous exchange solution can be selected over a broad range. Generally the weight ratio of ammonium compound to nickel and rare earth compounds combined is within the range of from about 0.05:1 to about 20:1, although a range of from about 0.2:1 to about 5:1 can be used with good results. The concentration of rare earth compounds in the aqueous exchange solution can be varied over a wide range and exchange conditions can be adjusted accordingly such that the rare earth content of the ion exchanged crystalline zeolite can be selected over a broad range. Generally, the content of the final catalyst composite in terms of the rare earth elements is from about 2 to about 25 weight percent. Preferably, the rare earth content of the catalyst can be within the range of from 5 to 20 weight percent. Good results were obtained employing a rare earth content ranging from about 9 to about 10 percent by weight. As noted above, the alkali metal content, for example sodium, of the exchanged catalyst support is partially removed by the ion exchange step and the alkali metal is generally from about 0.01 to about 2 percent by weight. Good results can be obtained employing an alkali metal content ranging from about 0.1 to about 1 percent by weight.

The nickel compounds which will be employed in admixture with the above-named rare earth metal compounds and ammonium compounds are those wherein the nickel ion is present in the cationic state. Some suitable compounds representative of the nickel compounds which can be used in the invention include the nitrates, bromides, acetates, chlorides, iodides, sulfates and mixtures thereof.

The nickel content in the final composition can also be selected over a broad range. Generally the composition will comprise from about 0.01 to about 12 weight percent nickel, although good results can be obtained employing a nickel content ranging from about 2 to about 7 percent by weight. Runs were actually carried out in which the nickel content ranged from 4 to 5 weight percent.

The procedure whereby the Type X and Type Y zeolites are treated with aqueous solutions of rare earth nickel and ammonium compounds to replace a portion of the alkali metal content of the zeolite is a cation exchange process which can be carried out in a batch or continuous fashion. Generally the exchange process is carried out on a continuous basis under the following typical conditions. A fixed bed of the zeolite material is treated with said aqueous solution of the rare earth, nickel and ammonium compounds at a temperature of 90° to 110° C. under conditions such that from about 0.1 to about 0.5 of the volume of aqueous salts solution per volume of zeolite is in contact with said zeolite per hour or, in other words, an LHSV ranging from about 0.1 to about 0.5 employed in the exchange process. Under these conditions, the exchange process can be completed in 48 hours or less to achieve the desired level of rare earth, nickel and ammonium ions in the zeolite. The exchange zeolite is then washed free of excess ions from the exchange step with water. The excess wash water is removed by drying the zeolite at a temperature ranging from about 100° C. to about 300° C. Just prior to calcination. The instant catalyst can be calcined before impregnation with the iridium compound to be described below or the impregnation can be carried out prior to the calcination step. In either case, the calcination is carried out by slowly heating the zeolite from about 100° C. to 200° C. to a temperature within the range of from about 200° to about 550° C. in order to calcine the zeolite and convert the ammonium cations to the hydrogen form. Usually, the calcination is conducted until a constant weight is obtained for the zeolitic material, generally from about 2 to about 10 hours. The calcined zeolite is then cooled in ambient air, i.e., under conditions of normal humidity.

Impregnation of the support with the iridium compound is carried out under what may be called "total impregnation" whereby the entire solids in the solution or dispersion of the iridium compound is used in the impregnation. Thus, all of the solids are left on the catalyst support and the liquid solvent or diluent for said iridium compound is simply removed by evaporation.

The content of iridium in the final catalyst composite is broadly from about 0.01 to about 1 weight percent and preferably from about 0.03 to about 0.25 weight percent.

A wide variety of iridium compounds can be employed in the impregnation step, such as the following compounds: iridium dioxide-$IrO_2$, iridium tricarbonylchloride dimer-$[Ir(CO)_3Cl]_2$, iridium trichloride-$IrCl_3$, iridium trichloride trihydrate-$IrCl_3.3H_2O$, bromocarbonylbis(triphenylphosphine)iridium(I)-$IrBr(CO)(Ph_3P)_2$, chlorocarbonylbis(triphenylphosphine)iridium(I)-$IrCl(CO)(Ph_3P_2)$, chloro-1,5-cyclooctadiene iridium(I) dimer-$[IrCl(1,5-C_8H_{12})]_2$, dicarbonylacetylacetanato iridium(I)-$Ir(CO)_2(C_5H_7O_2)$, and the like.

The composition described above is employed for the hydroalkylation of aromatic hydrocarbons to produce cycloalkyl aromatic hydrocarbons. Some of the feedstocks which are suitable for use in the present invention are aromatic compounds, i.e., monocyclic aromatic hydrocarbons and alkyl-substituted monocyclic aromatic hydrocarbons. Some specific examples of these are benzene, toluene, xylenes, and the like, and mixtures thereof. The aromatic hydrocarbon feedstocks should be essentially free of sulfur-containing compounds and other known poisons for hydrogenation catalysts in general. However, it is believed that a small amount of water, e.g., 20–50 ppm, in the feedstock is beneficial for maintaining catalyst activity over an extended period, e.g., several days.

The invention is particularly valuable for the conversion of benzene to cyclohexylbenzene. Cyclohexylbenzene is known as a valuable solvent and chemical intermediate. It can be converted in high yield to phenol and cyclohexanone by autooxidation with subsequent acid treatment. It is also useful as an intermediate in the production of cyclohexene which in turn can be utilized for the production of adipic acid and caprolactam.

The aromatic hydrocarbon feedstock is fed to the catalyst in a reaction zone operated under a wide range of conditions. The feedstock liquid hourly space velocity (LHSV), reaction temperature and pressure, and the hydrogen feed rate are not particularly critical; however, the liquid hourly space velocity (LHSV) generally ranges from about 1 to about 100, the reaction pressure generally ranges from about 345 to about 10,350 kPa (about 50 to about 1500 psig), the hydrogen feed rate generally ranges from about 0.1 to about 10 mole per mole of aromatic hydrocarbon feedstock per hour, and the reaction temperature generally ranges from about 100° to about 250° C. Based upon the runs described herein good results can be obtained employing a liquid hourly space velocity (LHSV) within the range of from about 5 to about 30, a reaction pressure within the range of from about 1,380 to about 4,830 kPa (about 200 to about 700 psig), the hydrogen feed rate within the range of from about 0.2 to about 1 mole per mole of aromatic hydrocarbon feed per hour, and the reaction temperature within the range of from about 150° to about 200° C.

The hydroalkylation reaction is conveniently carried out by having the above-described catalyst is a fixed bed reactor and then contacting said catalyst with the aromatic hydrocarbon feed and hydrogen in an upflow or downflow arrangement. It is also possible to employ a countercurrent flow of hydrogen and the aromatic hydrocarbon feed over the catalyst in the reaction zone. It is also possible to carry out the hydroalkylation reaction under batch conditions although a batch process is less preferred, because it is normally more expensive to operate and initial equipment costs are higher based upon the same size process.

Although a fixed bed reactor is mentioned above, most any type of reaction zone can be used as the particular type of reaction zone is not believed to be a critical parameter of the invention.

The reaction mixture from the reaction zone can usually be conveniently separated into the desired components by simple fractional distillation, and recycle of the unreacted feedstock and unreacted hydrogen can be accomplished as desired. The hydroalkylation products can be further purified as desired after separation from unreacted feedstock.

It is generally desirable to pretreat the catalyst with hydrogen gas prior to contacting the catalyst with the aromatic hydrocarbon in order to prereduce the catalyst. Based upon the runs described hereinafter, the hydrogen pressure and feed rate for the pretreating step generally is the same as that to be employed when contacting the aromatic hydrocarbon with the catalyst and the pretreating step generally takes from about 10 minutes to about 1 hour. In the hydroalkylation runs of the examples hereinafter described, conditions under which the catalyst was reduced and the reaction was carried out are indicated.

Further according to another aspect of the invention the catalysts as above described are treated with a small amount of a halogen-containing compound. Such a treatment of the catalyst compositions of the present invention was found to improve the selectivity of such compositions in hydroalkylation reactions. The compounds which can be utilized according to the instant invention as a source of halide include the elemental halogens themselves and the hydrohalides. Since treatment of the catalyst compositions of the invention with a compound was described above generally requires careful control of the addition reaction, it is preferred to employ a halogen-containing organic compound to treat the catalyst composition of the instant invention. A wide variety of such organic compounds can be employed to provide the necessary halide in the instant invention. These compounds can contain one or more atoms of halogen per molecule and the carbon content of such compounds is generally in the range of from about 1 to about 4 carbon atoms per molecule. For example, such compounds include alkyl halides, acid halides, or fully halogenated carbon compounds such as carbon tetrachloride or tetrachloroethylene. Examples of other suitable organic compounds which can be employed include chloroform, bromoform, dichloromethane, difluoromethane, dibromomethane, fluoromethane, chloromethane, bromomethane, 1,4-dichlorobutane, 1,4-dibromobutane, 1-chlorobutane, 1-fluorobutane, 1-bromobutane, 1,2-dichloroethane, 1,2-dibromoethane, 2-chloropropane, acetyl chloride, acetyl bromide, acetyl iodide, bromochloromethane, 1-bromo-4-chlorobutane, 1-fluoro-4-chlorobutane, 1,2-dichloroethylene, 1,2-dibromoethylene and mixtures thereof. The halogen-containing organic compounds in which the halogen component is bromine or chloride are preferred.

Although the catalysts of the present invention can be treated with halogen-containing compounds in various ways, one method is to simply add said halogen-containing compound to the aromatic hydrocarbon feed in the hydroalkylation process. The amount of halide added to the catalyst generally ranges from about 0.1 to about 100 milligrams of the elemental halogen per gram of catalyst utilized in the hydroalkylation reaction; however, good results can be obtained employing from about 0.5 to about 10 milligrams of the elemental halogen per gram of catalyst employed in the hydroalkylation reaction.

The addition of the halogen-containing compounds to the aromatic hydrocarbon feedstream can be utilized when the catalyst is fresh, i.e. previously unused, or can also be utilized after one or more regenerations of the above-mentioned catalyst. A typical regeneration procedure for the above-described catalyst includes purging the system of hydrogen with an inert gas such as nitrogen, then allowing air to enter the reaction zone and heating to a range of from about 400° to about 500° C. in the presence of flowing air and maintaining this temperature in the presence of flowing air for a total time of about three hours. The catalyst is then cooled in the presence of flowing air or nitrogen and at a temperature of about 200° C. is reduced with hydrogen as above described. The catalyst is then cooled to the desired reaction temperature and is then ready for use in the hydroalkylation reaction.

Although the compound or compounds which serve as the source of halide to modify the hydroalkylation catalyst of this invention can be added to the hydrocarbon feed in one portion, good results can be obtained by adding the halogen-containing compound to the feed over a period of from about 1 to about 3 hours. It is believed that a more efficient utilization of the halogen-containing compound is achieved by the above-described gradual addition of said compounds to the hydrocarbon feed in the process of this invention. It is to be understood that the halide treatment of the catalyst generally is only for a limited period of time and that the catalyst is then contacted with the feed in which no halogen-containing compound is added.

EXAMPLE I

Catalyst no. 1 was prepared in the following manner. A glass tube of 45 mm diameter which was equipped with heating means and means for passing an aqueous solution of compounds therethrough was charged with 424 grams of a Type X crystalline zeolite (Davison 13X molecular sieves of 8–12 mesh). The mole sieves charged to the cation exchange reactor were first treated by contacting with a slow stream of air over the weekend whereby the weight of the mole sieves increased from 350 grams to 424 grams. An aqueous solution of 400 grams of ammonium chloride, 100 grams of rare earth chlorides and 200 grams of nickel chloride hexahydrate in 4 liters of deionized water was prepared. The rare earth chlorides were obtained from the American Potash Corporation and had the following composition: $MCl_3 \cdot 6H_2O$ wherein M equals lanthanum 23%, cerium 43.5%, praseodymium 5.4%, neodymium 17.9%, samarium 1.9%, gadolinium 0.6%, and others 0.2%. The crystalline zeolite material was first wetted with a portion of the above solution and then charged to the tubular glass reactor described above and the remainder of the aqueous solution pumped through the crystalline zeolite bed at a rate of about 0.25 LHSV at a temperature of 96° C. The cation-exchanged zeolite was cooled, filtered, and washed six times with about 500 ml portions of deionized water and then allowed to dry in ambient air to give 512.3 grams of material. A portion (36.5 grams) of the cation-exchanged zeolite was impregnated with a solution of 0.0492 grams of iridium trichloride in about 80 ml of absolute ethanol. The ethanol was removed under reduced pressure on a rotary evaporator. An additional 50 ml of ethanol was added to wash the sides of the flask and this solvent was also removed in a manner similar to that previously described. The dried catalyst was then calcined by gradually raising the temperature overnight from room temperature to 204° C. in the presence of air and then increasing the temperature over an 8 hour period up to 517° C. The recovered calcined catalyst weighed 25 grams. The catalyst contained 0.10 weight percent iridium, and estimated contents of 4.6 weight percent nickel, 9.5 weight percent rare earths and 0.6 weight percent sodium.

Benzene Hydroalkylation

The catalyst (no. 1) described above was utilized in the hydroalkylation of benzene. In these hydroalkylation runs, a small tubular reactor equipped for continuous reaction operation was charged with 11.0 grams (15 ml) of the catalyst. The catalyst was prereduced at 170° C. for 30 minutes under 3,450 kPa (500 psig) at a hydrogen flow rate of 0.32 liters per minute. Other reaction conditions and the results obtained in this series of runs utilizing catalyst no. 1 are presented in Table I below. Run no. 3 of Table I was carried out after the catalyst had been regenerated by heating in air for 3.5 hours at about 480° C. Run no. 3 was also made after the catalyst had been contacted with feed containing 60 ppm of carbon tetrachloride over a period of 1 hour and 40 minutes. Run no. 5 was also made after the catalyst had been treated a second time with feed containing 50 ppm carbon tetrachloride over a 1 hour period. Hydrogen pressure in runs 1 and 3 was 3,450 kPa (500 psig) while in runs 2, 4, 5, 6 and 7, the pressure was 2,068 kPa (300 psig) and hydrogen flow rate was 0.32 liters per minute in runs 1 and 3 and 0.10 liters per minute in runs 2, 4 and 5. Hydrogen flow rate in run 6 was 0.18 l/min and 0.12 l/min in run 7.

Runs 6 and 7 were carried out after a tubular reactor equipped for continuous operation was charged with another portion 11.2 g (15 ml) of catalyst no. 1 which was then prereduced at 170° C. for 30 minutes under 2,068 kPa (300 psig) hydrogen at a flow rate of 0.10 liters per minute. Run 7 was made after the catalyst had been contacted with feed (500 ml) containing 100 ppm $CCl_4$ for 1.7 hr.

Table I

| Run No. | Temp. °C. | Benzene LHSV | Conv. % | Selectivity, Wt. % CH[a] | $C_{12}H_{22}$[b] | MCPB[c] | CHB[d] | Heavies[e] | Wt. Ratio CHB/CH |
|---|---|---|---|---|---|---|---|---|---|
| 1 | 167 | 20 | 10 | 66.4 | 1.60 | 0.40 | 22.1 | 9.9 | 0.33 |
| 2 | 176 | 16.5 | 10 | 57.3 | 1.57 | 0.60 | 32.3 | 8.0 | 0.56 |
| 3 | 177 | 18.7 | 12.4 | 22.5 | 0.48 | 1.61 | 66.9 | 8.0 | 3.0 |
| 4 | 169 | 20 | 7.8 | 17.2 | 0.19 | 0.82 | 68.7 | 12.8 | 4.0 |
| 5 | 164 | 20 | 3.7 | 11.5 | tr. | 0.48 | 75.0 | 13.5 | 6.5 |
| 6 | 195 | 20 | 10.8 | 44.9 | 0.55 | 0.87 | 49.0 | 4.6 | 1.1 |
| 7 | 184 | 20 | 8.0 | 27.4 | 0.30 | 3.79 | 64.6 | 4.0 | 2.4 |

[a]CH = Cyclohexane.
[b]$C_{12}H_{22}$ = Compounds of the indicated general formula including bicyclohexyl.
[c]MCPB = Methylcyclopentylbenzene.
[d]CHB = Cyclohexylbenzene
[e]Heavies = Mixture of compounds greater than $C_{12}H_{22}$.

The results shown in Table I were obtained from gas-liquid phase chromatography (GLC) analysis of samples from the effluent of the hydroalkylation reaction zone and from distillation results on a combination of several consecutive samples, e.g. for heavies analysis.

EXAMPLE II

Catalyst Preparation

Catalyst no. 2 was prepared utilizing 36.5 grams of a Type X (Davison 13X molecular sieve) crystalline zeolite which had been cation exchanged in essentially the same manner as that described for the support in the preparation of catalyst no. 1 of Example 1. The cation-exchanged crystalline zeolite was impregnated with a solution of 0.0241 grams of iridium trichloride in about 80 ml of absolute ethanol. The ethanol was removed on a rotary evaporator and the catalyst dried in air. The catalyst material was then calcined by maintaining it for 3 days at 200° C. after which it was then placed in a muffle furnace and heated for about 5.25 hours up to a maximum temperature of 520° C. The catalyst was cooled and removed to an air tight container. Catalyst no. 2 thus contained 0.05 weight percent iridium, and estimated contents of 4.6 weight percent nickel, 9.5 weight percent rare earths and 0.6 weight percent sodium.

Benzene Hydroalkylation

A tubular reactor equipped for continuous operation was charged with 11.3 grams (15 ml) of catalyst no. 2 prepared as described above. The catalyst was prereduced in the reactor at 175° C. under 2,068 kPa (300 psig) hydrogen at a hydrogen flow rate of 0.10 liters per minute for a period of 15 minutes. Hydrogen pressure in run 14 of Table II below was at 3,450 kPa (500 psig) while runs 8 through 13 were carried out under hydrogen pressure of 2,068 (300 psig). All of the runs utilized a hydrogen flow rate of 0.10 liters per minute. Run no. 9 was conducted after the catalyst had been contacted with benzene feed containing 100 parts per million of carbon tetrachloride for a period of 1 hour. Run no. 10 was conducted after the catalyst had been regenerated by burning off in air at about 530° for a period of about 2.25 hours. Run no. 11 was conducted after the catalyst had been contacted for 15 minutes with benzene feed containing 100 parts per million carbon tetrachloride. The results of runs 8 through 14 and other reaction conditions utilized in said runs are presented below in Table II. The methods for obtaining the results in Table II were the same as those utilized in Example I.

3,450 kPa and 2,068 kPa hydrogen pressure (compare runs 1 with 3 and 2 with 4 and also run 8 with 9).

I claim:

1. A process for producing cycloalkyl aromatic hydrocarbons which comprises contacting at least one aromatic hydrocarbon under hydroalkylation conditions and in the presence of hydrogen with a catalyst consisting essentially of iridium supported on a calcined, acidic, nickel and rare earth-treated crystalline zeolite.

2. A process according to claim 1 wherein the catalyst is treated with hydrogen prior to being contacted with the aromatic hydrocarbon to increase the activity of said catalyst for said contacting.

3. A process according to claim 1 wherein aromatic hydrocarbon feed for said contacting contains from about 5 to about 50 ppm of water to maintain catalyst activity over an extended period.

4. A process according to claim 1 wherein aromatic hydrocarbon is contacted with said catalyst and a liquid hourly space velocity ranging from about 1 to about 100, a hydrogen pressure ranging from about 345 to about 10,350 kilopascals (50 to 1500 psig), a hydrogen feed rate ranging from about 0.1 to about 10 moles per hour of hydrogen per mole of aromatic hydrocarbon, a temperature ranging from about 100° to about 250° C.

5. A process according to claim 1 wherein the catalyst is treated with a halogen-containing compound in an amount sufficient to promote the formation of a desired cycloalkyl aromatic hydrocarbon when said composition is employed in a hydroalkylation reaction.

6. A process according to claim 1 wherein said aromatic hydrocarbon is benzene which is converted to cyclohexylbenzene.

Table II

| Run No. | Temp. °C. | Benzene | | Selectivity, Wt. % | | | | | Wt. Ratio CHB/CH |
|---|---|---|---|---|---|---|---|---|---|
| | | LHSV | Conv. % | CH | $C_{12}H_{22}$ | MCPB | CHB | Heavies | |
| 8 | 175 | 18.7 | 10.7 | 20.5 | 0.35 | 0.85 | 68.1 | n.a.[a] | 3.3 |
| 9 | 166 | 22 | 8.5 | 11.0 | 0.35 | 0.84 | 77.6 | 9.4 | 7.0 |
| 10 | 189 | 20 | 13.0 | 20.7 | 0.55 | 1.59 | 71.2 | n.a. | 3.4 |
| 11 | 180 | 20 | 11.2 | 7.8 | 0.13 | 1.58 | 83.8 | 6.6 | 10.8 |
| 12 | 170 | 20 | 10.6 | 8.2 | 0.17 | 1.32 | 82.7 | 7.6 | 10.1 |
| 13 | 160 | 20 | 10.2 | 9.2 | tr. | 0.96 | 84.0 | 5.4 | 9.2 |
| 14 | 161 | 20 | 13.2 | 13.8 | 0.46 | 0.75 | 76.0 | 9.0 | 5.5 |

[a]n.a. = No analysis made.

Examination of the runs presented in Tables I and II indicates that catalyst no. 2 was more selective toward cyclohexylbenzene than catalyst no. 1 even though catalyst no. 1 contained a higher level of iridium (compare run 2 with run 8 and run 4 with run 12). The very good selectivity to cyclohexylbenzene at the low level of iridium in the hydroalkylation catalysts indicates a highly productive catalyst and also tends to decrease the cost of hydroalkylation catalysts based on iridium. It can also be noted that small amounts of carbon tetrachloride serve to increase the selectivity of the catalyst of the instant invention to cyclohexylbenzene at both 7. A process according to claim 1 wherein the total iridium content ranges from about 0.01 to about 1 weight percent and the crystalline zeolite is selected from the group consisting of Type X and Type Y zeolites.

8. A process according to claim 1 wherein said aromatic hydrocarbon is benzene and said catalyst is prereduced to contacting with hydrogen prior to contacting with aromatic hydrocarbon and the catalyst contains from about 0.03 to about 0.25 weight percent iridium.

* * * * *